US00PP16999P2

(12) United States Plant Patent
Vandenberg

(10) Patent No.: US PP16,999 P2
(45) Date of Patent: Aug. 15, 2006

(54) ***CHRYSANTHEMUM* PLANT NAMED 'YOIDEA'**

(50) Latin Name: *Chrysanthemum×morifolium*
Varietal Denomination: Yoidea

(75) Inventor: Cornelis P. Vandenberg, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 11/122,822

(22) Filed: May 5, 2005

(51) Int. Cl.
*A01H 5/00* (2006.01)

(52) U.S. Cl. ..... Plt./295

(58) Field of Classification Search ..... Plt./295
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Chrysanthemum* plant named 'Yoidea', characterized by its upright cut *Chrysanthemum* that is usually grown as a natural spray; dark green-colored foliage; freely flowering habit; uniform inflorescence form and development; large daisy-type inflorescences; bright yellow-colored ray florets; response time about 9.5 weeks; strong peduncles; and good postproduction longevity.

2 Drawing Sheets

Botanical designation: *Chrysanthemum×morifolium.*
Cultivar denomination: 'Yoidea'.

BACKGROUND OF THE INVENTION

The present invention relates to a new and distinct cultivar of *Chrysanthemum* plant, botanically known as *Chrysanthemum×morifolium* and hereinafter referred to by the name 'Yoidea'.

The new *Chrysanthemum* is a product of a planned breeding program conducted by the Inventor in Salinas, Calif. and Alva, Fla. The objective of the breeding program is to create new cut *Chrysanthemum* cultivars having inflorescences with desirable colors and good inflorescence form and substance.

The new *Chrysanthemum* originated from a cross-pollination made by the Inventor in January, 1998, in Salinas, Calif., of a proprietary selection of *Chrysanthemum×morifolium* identified as code number K062, not patented, as the female, or seed, parent with a proprietary selection of *Chrysanthemum×morifolium* identified as code number K101, not patented, as the male, or pollen, parent.

The cultivar Yoidea was discovered and selected by the Inventor as a flowering plant within the progeny of the stated cross-pollination in a controlled environment in Alva, Fla., in March, 1999. The selection of this plant was based on its desirable inflorescence color and good inflorescence form and substance.

Asexual reproduction of the new *Chrysanthemum* by terminal cuttings in a controlled environment in Alva, Fla. since May, 1999, has shown that the unique features of this new *Chrysanthemum* are stable and reproduced true to type in successive generations.

SUMMARY OF THE INVENTION

Plants of the cultivar Yoidea have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yoidea'. These characteristics in combination distinguish 'Yoidea' as a new and distinct cultivar:

1. Upright cut *Chrysanthemum* that is usually grown as a natural spray.
2. Dark green-colored foliage.
3. Freely flowering habit, about ten inflorescences per flowering stem.
4. Uniform inflorescence form and development.
5. Large daisy-type inflorescences that are about 8.5 cm in diameter.
6. Attractive bright yellow-colored ray florets.
7. Response time about 9.5 weeks.
8. Strong peduncles.
9. Good postproduction longevity with inflorescences and foliage maintaining good substance and color for about 17 days in an interior environment.

Compared to plants of the female parent selection, plants of the new *Chrysanthemum* have bright yellow-colored ray florets whereas plants of the female parent selection have white-colored ray florets.

Compared to plants of the male parent selection, plants of the new *Chrysanthemum* have shorter flowering stems, more ray florets per inflorescence and longer peduncles. In addition, plants of the new *Chrysanthemum* and the male parent selection differ in ray floret coloration as plants of the male parent selection have white-colored ray florets.

Plants of the new *Chrysanthemum* can be compared to plants of the *Chrysanthemum×morifolium* cultivar Arango, disclosed in U.S. Plant Pat. No. 14,619. In side-by-side comparisons conducted in Alva, Fla., plants of the new *Chrysanthemum* differed from plants of the cultivar Arango in the following characteristics:

1. Plants of the new *Chrysanthemum* had shorter flowering stems than plants of the cultivar Arango.
2. Plants of the new *Chrysanthemum* had more uniform flowering than plants of the cultivar Arango.
3. Plants of the new *Chrysanthemum* flowered about eight days earlier than plants of the cultivar Arango.
4. Plants of the new *Chrysanthemum* had shorter peduncles than plants of the cultivar Arango.

BRIEF DESCRIPTION OF THE PHOTOGRAPHS

The accompanying colored photographs illustrate the overall appearance of the new *Chrysanthemum,* showing the colors as true as it is reasonably possible to obtain in colored reproductions of this type. Colors in the photographs may differ slightly from the color values cited in the detailed botanical description which accurately describe the colors of the new *Chrysanthemum.*

The photograph on the first sheet comprises a side perspective view of a typical flowering stem of 'Yoidea' grown as a natural spray.

The photograph on the second sheet comprises a close-up view of typical inflorescences of 'Yoidea'.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown in Salinas, Calif., under conditions which approximate commercial practice in a polyethylene-covered greenhouse. Two-week old rooted cuttings were planted on Nov. 3, 2004 and received four weeks of long day/short nights followed by short day/long nights until flowering. Plants were grown as single-stem natural spray cut *Chrysanthemums.* During the production time, the following environmental conditions were measured: day temperatures, 24 to 27° C.; night temperatures, 10 to 16° C.; and light levels, 2,000 to 4,000 foot-candles. Measurements and numerical values represent averages for six to ten typical flowering stems and were taken about ten weeks after the start of short days.

Botanical classification: *Chrysanthemum×morifolium* cultivar Yoidea.

Commercial classification: Daisy-type cut *Chrysanthemum.*

Parentage:

*Female or seed parent.*—Proprietary selection of *Chrysanthemum×morifolium* identified as code number K062, not patented.

*Male or pollen parent.*—Proprietary selection of *Chrysanthemum×morifolium* identified as code number K101, not patented.

Propagation:

*Type.*—Terminal tip cuttings.

*Time to rooting.*—About 10 to 14 days with soil temperatures of 18 to 21° C.

*Root description.*—Fine, fibrous; white in color.

*Rooting habit.*—Freely branching.

Plant description:

*Appearance.*—Herbaceous daisy-type cut flower that is typically grown as a natural spray.

*Flowering stem description.*—Aspect: Erect. Length: About 104 cm. Spray diameter: About 17.5 cm. Stem diameter: About 8 mm. Internode length: About 3.4 cm. Texture: Pubescent; longitudinally ridged. Color: Close to 146A.

*Foliage description.*—Arrangement: Alternate. Length: About 7.6 cm. Width: About 3.8 cm. Apex: Cuspidate. Base: Attenuate. Margin: Palmately lobed; sinuses parallel to divergent. Texture: Upper and lower surfaces, pubescent and leathery; veins prominent on lower surface. Color: Developing and fully expanded foliage, upper surface: Close to 147A. Developing and fully expanded foliage, lower surface: Close to 147B. Venation, upper surface: Close to 147A. Venation, lower surface: Close to 146A. Petiole: Length: About 1.8 cm. Diameter: About 2 mm. Texture, upper and lower surfaces: Pubescent. Color, upper and lower surfaces: 146A to 146B.

Flowering description:

*Appearance.*—Daisy-type inflorescence form with elongated oblong-shaped ray florets. Inflorescences borne on terminals, arising from leaf axils. Disc and ray florets develop acropetally on a capitulum.

*Flowering response.*—Under natural conditions, plant flower in the autumn/winter in the Northern Hemisphere. At other times of the year, inflorescence initiation and development can be induced under short day/long night conditions (at least 13.5 hours of darkness). Plants exposed to three to four weeks of long day/short night conditions after planting followed by photoinductive short day/long night conditions flower about 9.5 weeks later when grown as a natural spray. Inflorescences uniform in form and development.

*Postproduction longevity.*—In an interior environment, inflorescences and foliage will maintain good color and substance for about 17 days in an interior environment.

*Quantity of inflorescences.*—Freely flowering habit, about ten inflorescences per stem develop.

*Fragrance.*—Faint; sweet.

*Inflorescence size.*—Diameter: Large, about 8.5 cm. Depth (height): About 3.1 cm. Disc diameter: About 1.9 cm. Receptacle diameter: About 7 mm. Receptacle height: About 9 mm.

*Inflorescence buds.*—Height: About 8 mm. Diameter: About 1 cm. Shape: Oblate. Color: Close to 146A to 147A.

*Ray florets.*—Shape: Elongated oblong. Length: About 4.25 cm. Width: About 1 cm. Corolla tube length: About 7.5 mm. Apex: Acute to emarginate. Base: Fused. Texture: Smooth, glabrous; satiny; longitudinally ridged. Aspect: Initially erect; when mature, mostly straight and about 45° from vertical. Number of ray florets per inflorescence: About 57 in about three whorls. Color: When opening and fully opened, upper surface: 6A. When opening and fully opened, lower surface: 6A to 6B.

*Disc florets.*—Shape: Tubular, elongated. Length: About 8 mm. Width, apex: About 2.5 mm. Width, base: About 2 mm. Number of disc florets per inflorescence: About 127. Color: Immature: Close to 144A. Mature: Apex: Close to 9A. Mid-section: Close to 154D. Base: Close to 155D.

*Phyllaries.*—Quantity per inflorescence: About 28 in about two to three whorls. Length: About 9 mm. Width: About 3.5 mm. Shape: Lanceolate. Apex: Acute. Base: Truncate. Margin: Entire. Texture, upper surface: Smooth, waxy. Texture, lower surface: Pubescent. Color, upper surface: Close to 144A to 146A. Color, lower surface: Close to 146A to 147A.

*Peduncles.*—Length: First peduncle: About 10 cm. Fourth peduncle: About 14.5 cm. Seventh peduncle: About 21 cm. Diameter: About 3.5 mm. Angle: About 40 to 45° from vertical. Strength: Strong. Texture: Pubescent. Color: Close to 146A.

*Reproductive organs.*—Androecium: Present on disc florets only. Anther length: Less than 1 mm. Anther color: Close to 15A. Amount of pollen: None observed. Gynoecium: Present on both ray and disc florets. Style length: About 6 mm. Style color: Close to 144C to 144D. Stigma color: Close to 9A.

*Seed/fruit.*—Seed and fruit production has not been observed.

Disease/pest resistance: Resistance to pathogens and pests common to *Chrysanthemums* has not been observed on plants grown under commercial conditions.

Temperature tolerance: Plants of the new *Chrysanthemum* have demonstrated good tolerance to low temperatures of 7° C. and high temperatures high temperatures of 38° C.

It is claimed:

1. A new and distinct cultivar of *Chrysanthemum* plant named 'Yoidea', as illustrated and described.

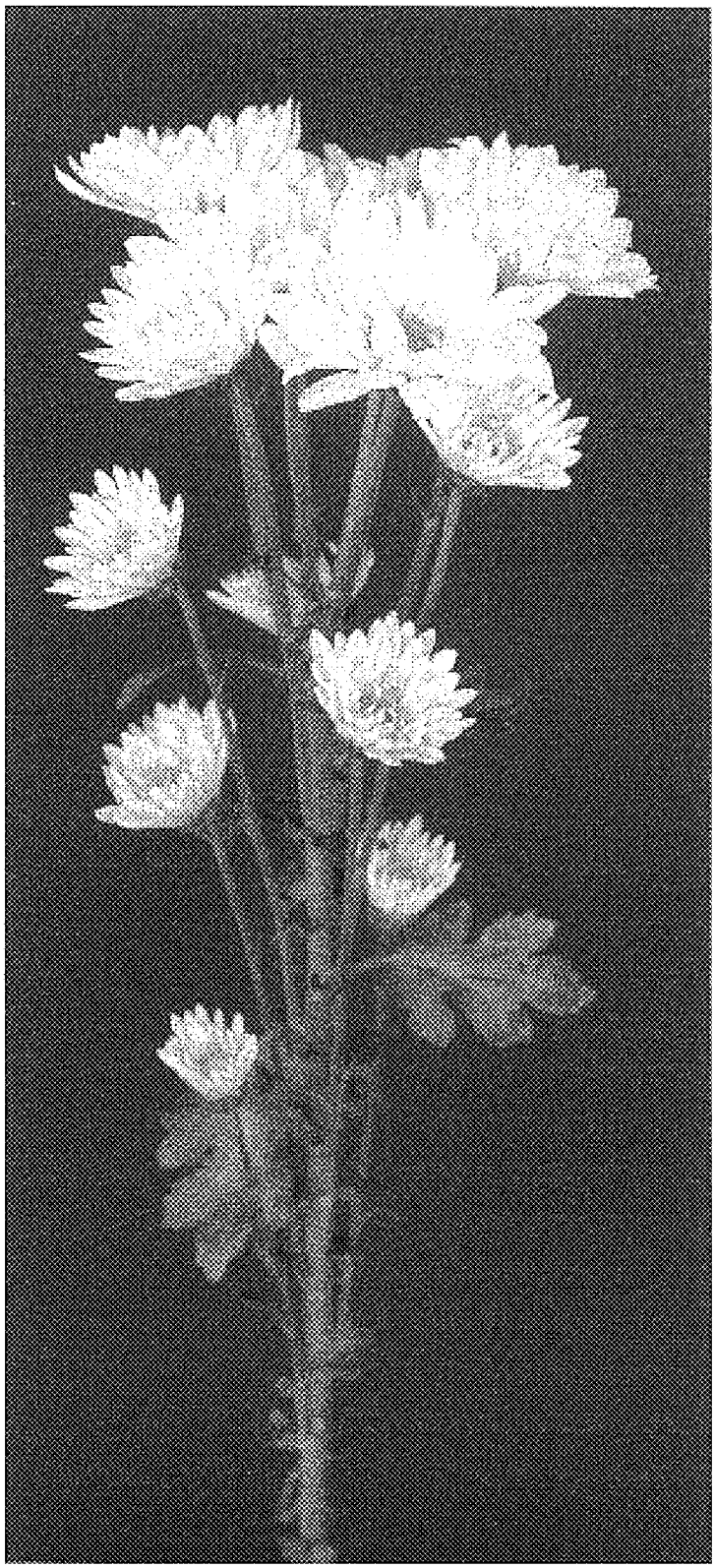

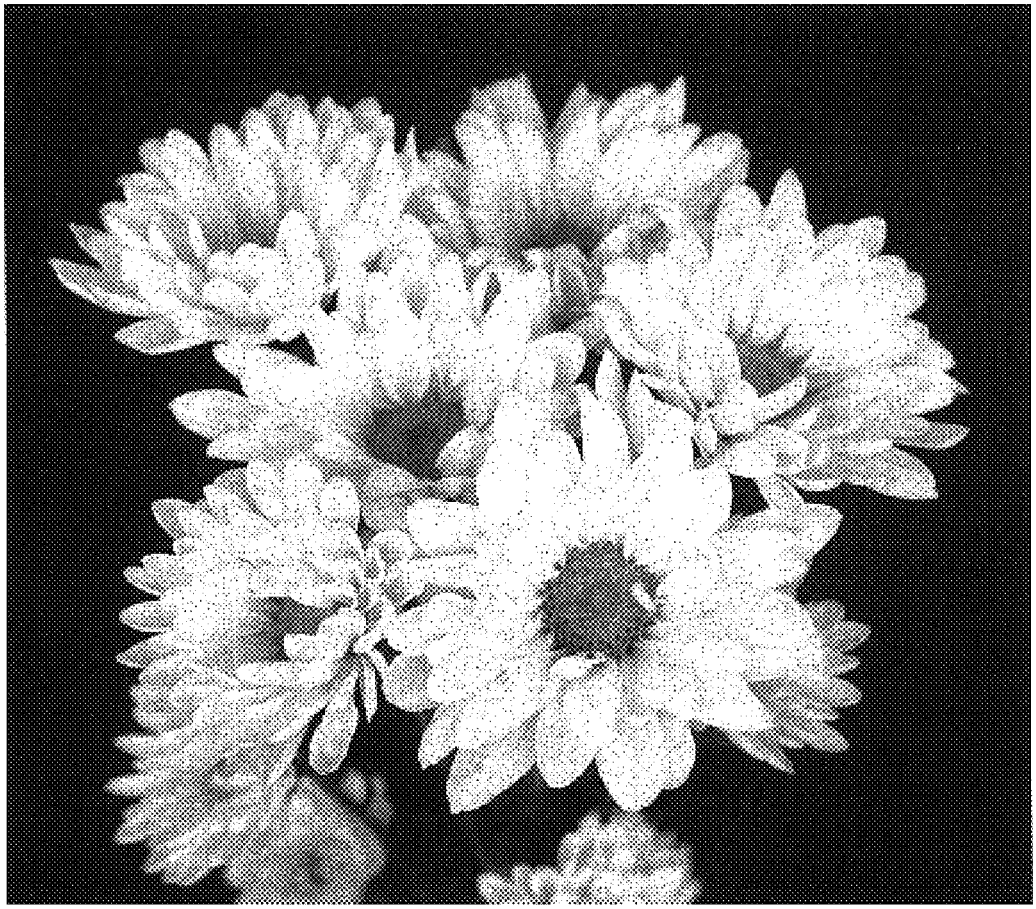

* * * * *